United States Patent
Clyde et al.

(10) Patent No.: US 6,544,405 B2
(45) Date of Patent: Apr. 8, 2003

(54) SENSOR COATING INHIBITING GLASS FORMATION

(75) Inventors: Eric P. Clyde, Bay City, MI (US); Paul Kikuchi, Fenton, MI (US); Richard F. Beckmeyer, Davisburg, MI (US); William J. LaBarge, Bay City, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/739,520

(22) Filed: Dec. 15, 2000

(65) Prior Publication Data

US 2002/0104765 A1 Aug. 8, 2002

(51) Int. Cl.$^7$ .............................. G01N 27/407
(52) U.S. Cl. ............... 205/784.5; 204/424; 204/429
(58) Field of Search ..................... 204/421–429; 205/783–785

(56) References Cited

U.S. PATENT DOCUMENTS

| | | | |
|---|---|---|---|
| 3,941,673 A | * | 3/1976 | Takao et al. |
| 4,304,652 A | | 12/1981 | Chiba et al. |
| 4,379,741 A | | 4/1983 | Sano et al. |
| 4,818,364 A | | 4/1989 | Weber et al. |
| 5,139,639 A | | 8/1992 | Holleboom |
| 5,271,821 A | * | 12/1993 | Ogasawara et al. |
| 5,360,528 A | | 11/1994 | Oh et al. |
| 5,384,030 A | | 1/1995 | Duce et al. |
| 5,423,972 A | | 6/1995 | Mann et al. |
| 5,762,737 A | | 6/1998 | Bloink et al. |
| 5,849,165 A | * | 12/1998 | Kojima et al. |

OTHER PUBLICATIONS

Haaland, "Noncatalytic Electrode for Solid–Electrolyte Oxygen Sensors", J. of the Electrochemical Soc., Apr. 1980, vol. 127, No. 4, pp. 796–804, XP–002084798 ISSN 0013–4651, pp. 796–804.*
U.S. patent application Ser. No. 09/741,662, Donelon et al., filed Dec. 19, 2000.

* cited by examiner

*Primary Examiner*—T. Tung
(74) *Attorney, Agent, or Firm*—Vincent A. Cichosz

(57) ABSTRACT

An exhaust gas sensor element having an electrochemical cell, a protective material in fluid communication with the electrochemical cell, and a reactive inhibitive coating disposed over the protective material. The reactive inhibitive coating prevents the reaction of compounds with acids(e.g., phosphates) in the exhaust gas, which may form a dense glass layer on the outside of the gas sensor. The reactive inhibitive coating is either an alkaline earth oxide ethoxide, and/or carbonate that is deposited on the gas sensor to a thickness so as to preferably provide an excess of either the alkaline earth material.

12 Claims, 1 Drawing Sheet

SENSOR COATING INHIBITING GLASS FORMATION

TECHNICAL FIELD

This invention relates to gas sensors, and, more particularly, to oxygen sensors that inhibit glass formation thereon.

BACKGROUND OF THE INVENTION

Oxygen sensors are used in a variety of applications that require qualitative and quantitative analysis of gases. In automotive applications, the direct relationship between the oxygen concentration in the exhaust gas and the air-to-fuel ratio of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor typically comprises an ionically conductive solid electrolyte material, a porous electrode on the exterior surface of the electrolyte exposed to the exhaust gases with a porous protective overcoat, and an electrode on the interior surface of the sensor exposed to a known oxygen partial pressure. Sensors typically used in automotive applications use a yttria stabilized zirconia based electrochemical galvanic cell with platinum electrodes, which operate in potentiometric mode to detect the relative amounts of oxygen present in the exhaust of an automobile engine. When opposite surfaces of this galvanic cell are exposed to different oxygen partial pressures, an electromotive force is developed between the electrodes on the opposite surfaces of the zirconia wall, according to the Nernst equation:

$$E = \left(\frac{RT}{4F}\right)\ln\left(\frac{P_{O_2}^{ref}}{P_{O_2}}\right)$$

where:
E=electromotive force
R=universal gas constant
F=Faraday constant
T=absolute temperature of the gas
$p_{O_2}^{ref}$=oxygen partial pressure of the reference gas
$P_{O_2}$=oxygen partial pressure of the exhaust gas Due to the large difference in oxygen partial pressure between fuel rich and fuel lean exhaust conditions, the electromotive force changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture.

In automotive applications employing oxygen sensors, data gathered by sensors is quantified and used to adjust the air-to-fuel ratio of the fuel mixture as it is fed in the engine. However, the performance of an oxygen sensor can be altered by the presence of poisons, which are generally the reaction products of components of the exhaust gas of the automotive system. These poisons typically result from the absorption of volatiles in the engine oil that either proceed directly into the combustion process or are revolatilized when the engine approaches its operating temperature. The poison vapors are drawn into the combustion chamber of the engine through the Positive Crankcase Ventilation (PCV) system and are then oxidized or reacted to form a smoke that contains molecule-sized particles. These particles travel in the exhaust gas and deposit on the surface of the oxygen sensor.

One type of poison is the deposition of impervious glass materials on the sensor surface, which often significantly impairs the reliability of the sensor element. These poisons form dense glass phases on the surface of the sensor and inhibit sensor performance. Typically, only a limiting amount of metallic particulates are present in the exhaust stream, and CaO and $ZnO_2$ react with phosphates in the exhaust stream to form dense glass phases of $CaPO_4$ and $Zn(PO_4)_2$. The formation of dense glass phases, which are deposited onto the surface of the sensor element, cause the time for particles to diffuse through the sensor element to increase significantly. This increase in diffusion time, in turn, causes $NO_x$ emissions to increase significantly, and causes a delay in the response of the system in adjusting the air-to-fuel ratio of the fuel mixture as it is fed to the engine.

What is needed in the art is a sensor element that inhibits the formation of dense glass phases of $CaPO_4$ and $Zn_3(PO_4)_2$.

SUMMARY OF THE INVENTION

The drawbacks and disadvantages of the prior art are overcome by the gas sensor element and method for its use. The gas sensor element, comprises: an electrochemical cell, a protective material in fluid communication with the electrochemical cell, and an inhibitive coating. The inhibitive coating, which is disposed on a side of the protective material opposite the electrochemical cell, comprises an alkaline earth material.

The method of operating the gas sensor element, comprises: exposing the gas sensor element to an exhaust gas. The exhaust gas is diffused through the inhibitive coating to the electrochemical cell where a constituent of the gas is sensed. Additionally, acid gases in the exhaust gas are reacted with the inhibitive coating.

The above-described and other features and advantages gas sensor and method for its use will be appreciated and understood by those skilled in the art from the following detailed description, drawings, and appended claims.

BRIEF DESCRIPTION OF THE DRAWINGS

The apparatus and method will now be described by way of example, with reference to the accompanying drawing, which is meant to be exemplary, not limiting.

The FIGURE is an exploded view of an embodiment of a planar gas sensor element having a protective surface layer disposed thereon.

DETAILED DESCRIPTION OF THE INVENTION

Figure 1:
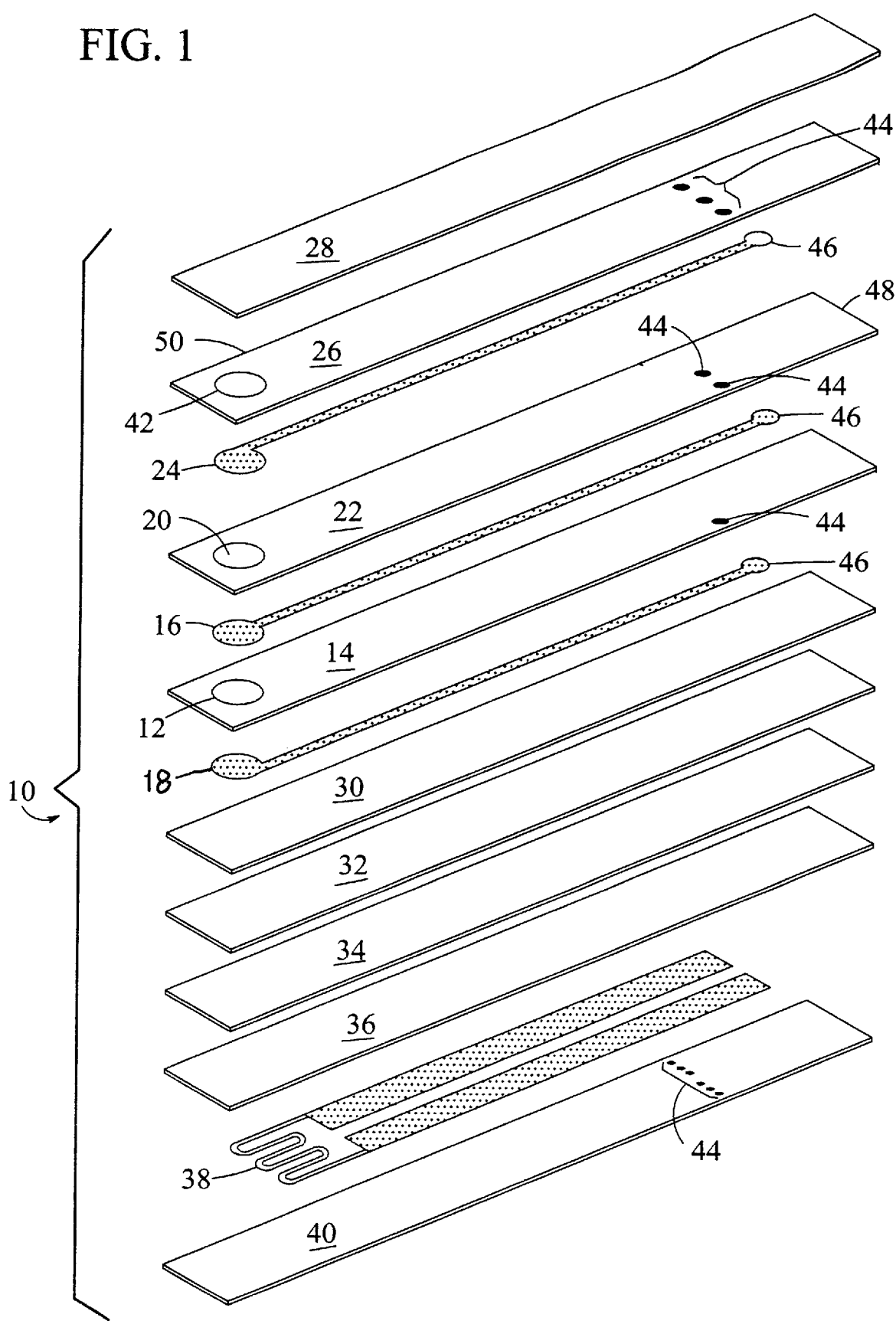

A gas sensor is described herein, wherein an inhibitive coating comprising a surface layer of an alkaline earth material is disposed thereon to prevent the formation of dense glass phases on the surface of the sensor as a result of the reaction of acid gases with particulates such as CaO or $ZnO_2$. Although conventional sensors typically have an alumina ($Al_2O_3$) layer disposed on one side of the sensor adjacent to the outer electrode, this layer fails to limit dense glass formation. The gas sensor described below utilizes a separate surface layer of an alkaline earth material to flux the phosphate ions deposited from the exhaust stream. It is hereby understood that although the apparatus is described in relation to making a linear oxygen sensor, the sensor could be conical and/or could be a stoichiometric sensor, a nitrous oxide sensor, a hydrogen sensor, a hydrocarbon sensor, or a similar apparatus.

Referring to the FIGURE, one embodiment of the arrangement of the different layers of a sensor element is shown generally at 10. Sensor element 10 comprises: a solid electrolyte 12 disposed in a dielectric layer 14, with an inner electrode 16 and a reference electrode 18 disposed on opposite sides of solid electrolyte 12; a porous electrolyte 20 disposed in electrical communication with inner electrode 16 and disposed in a dielectric layer 22; an outer electrode 24 disposed on the side of porous electrolyte 20 opposite inner electrode 16; a dielectric layer 26 disposed against dielectric layer 22 opposite dielectric layer 14 with a protective material 42 disposed therein, in fluid communication with outer electrode 24, and an inhibitive coating 28 disposed against dielectric layer 26. Sensor element 10 further comprises internal support layers 30, 32, 34, 36 disposed against dielectric layer 14; a heater 38 disposed between support layer 36 and a protective outer layer 40; vias 44 formed in dielectric layers 14, 22, 26, and outer layer 40; leads 46 in electrical communication with electrodes 16, 18, 24; a terminal end 48; and a sensor end 50. It is understood that conventional components such as a lead gettering layer, ground plane, etc. can also be employed.

Dielectric layers 14, 22, 26 support layers 30, 32, 34, 36, and outer layer 40 typically comprise alumina or a similar material that is capable of inhibiting electrical communication and providing physical protection. Preferably, layers 14, 22, 26, 30, 32, 34, 36 used in the manufacture of sensor element 10 comprise a material having substantially similar coefficients of thermal expansion, shrinkage characteristics, and chemical compatibility in order to minimize, if not eliminate, delamination and other processing problems.

Outer electrode 24, porous electrolyte 20, and inner electrode 16 form a pumping cell, while inner electrode 16, solid electrolyte 12, and reference electrode 18 form a reference cell. Oxygen in the exhaust enters the pumping cell through inhibitive coating 28 and protective material 42, and diffuses through outer electrode 24 and porous electrolyte 20 to inner electrode 16, where the oxygen is ionized and pumped back out of the cell. Generally, a reference cell is used in combination with the pumping cell, but the pumping cell can be used as the only electrochemical cell in the sensor in lean-only applications. The reference cell is used to compare the partial pressure of oxygen at inner electrode 16 with a known oxygen partial pressure at reference electrode 18 in order to determine the potential that should be applied to the pumping cell. The measured current in the pumping cell will be proportional to the partial pressure of oxygen in the exhaust gas.

Solid electrolyte layer 12 can be any material that is capable of permitting the electrochemical transfer of oxygen ions while inhibiting the physical passage of exhaust gases, has an ionic/total conductivity ratio of approximately unity, and is compatible with the environment in which sensor element 10 will be utilized (e.g., up to about 1,000° C.). Possible solid electrolyte materials include can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as combinations comprising at least one of the foregoing materials. For example, the electrolyte can be alumina and yttrium stabilized zirconia. Typically, the solid electrolyte has a thickness of up to about 500 microns, with a thickness of approximately 25 microns to about 500 microns preferred, and a thickness of about 50 microns to about 200 microns especially preferred.

As with solid electrolyte 12, porous electrolyte 20 makes use of an applied electrical potential to influence the movement of oxygen. Porous electrolyte 20 should be capable of permitting the physical migration of exhaust gas and the electrochemical movement of oxygen ions, and should be compatible with the environment in which sensor 10 is utilized. Typically, porous electrolyte 20 has a porosity of up to about 20%, with a median pore size of up to about 0.5 microns, or, alternatively, comprises a solid electrolyte having one or more holes, slits, or apertures therein, so as to enable the physical passage of exhaust gases. Commonly assigned U.S. Pat. No. 5,762,737 to Bloink et al., which is hereby incorporated in its entirety by reference, further describes porous electrolytes that may be useful in the instant application. Possible porous electrolytes include those listed above for solid electrolyte 12.

Electrolytes 12, 20 can be formed via many conventional processes including, but not limited to, die pressing, roll compaction, stenciling and screen printing, and the like. For improved process compatibility, it is preferred to utilize a tape process using known ceramic tape casting methods.

The various electrode 16, 18, 24 disposed in contact with solid electrolyte 20 and porous electrolyte 20 can comprise any catalyst capable of ionizing oxygen, including, but not limited to, metals such as platinum, palladium, osmium, rhodium, iridium, gold, and ruthenium; metal oxides-such as zirconia, yttria, ceria, calcia, alumina and the like; other materials, such as silicon, and the like; and mixtures and alloys comprising at least one of the foregoing catalysts. Electrode 24 preferably has a porosity sufficient to permit the diffusion of oxygen molecules without substantially restricting such gas diffusion. Typically, the porosity is greater than the porosity of porous electrolyte 20.

With respect to the size and geometry of electrodes 16, 18, 24, they are generally adequate to provide current output sufficient to enable reasonable signal resolution over a wide range of air/fuel ratios while preventing leakage between electrolytes 12, 20. Generally, a thickness of about 1.0 microns to about 25 microns can be employed, with a thickness of about 5 microns to about 20 microns preferred, and about 10 microns to about 18 microns more preferred. The geometry of the electrodes is preferably substantially similar to the geometry of the electrolyte, with at least a slightly larger overall size than the electrolyte preferred to ensure that the electrodes cover the electrolyte, thereby preventing leakage between electrolytes and allowing sufficient print registration tolerance.

Electrodes 16, 18, 24 can be formed using conventional techniques such as sputtering, chemical vapor deposition, screen printing, and stenciling, among others, with screen printing electrodes 16, 18, 24 onto appropriate tapes being preferred due to simplicity, economy, and compatibility with the subsequent co-fired process. For example, reference electrode 18 can be screen printed onto support layer 30 or over the solid electrolyte 12, inner electrode 16 can be screen printed over solid electrolyte 12 or porous electrolyte 20, and outer electrode 24 can be screen printed over porous electrolyte 20 or protective material 42. Electrode leads 46 and vias 44 in the alumina layers are typically formed simultaneously with electrodes.

Although the porosity of reference electrode 18 is typically sufficient to hold an adequate quantity of oxygen to act as a reference, a space for storing reference oxygen (not shown) can be provided between reference electrode 18 and adjoining support layer 30. This space can be formed by depositing a carbon base material, i.e., a fugitive material such as carbon black, between reference electrode 18 and layer 30 such that upon processing the carbon burns out, and leaves a void. Alternatively, reference electrode 18 can be in fluid communication with a point external to the sensor allowing air access to the reference electrode 18 via a channel (not shown) in layer 30.

Electrolytes 12, 20 and protective material 42 can be attached to dielectric layers 14, 22, 26. Electrolytes 12, 20 and protective material 42 can optionally be formed as inserts within dielectric layers 14, 24, 26, rather than in separate layers as is conventionally known in the art. This arrangement eliminates the use of excess porous electrolyte, solid electrolyte, and protective material, and reduces the size of sensor element 10 by eliminating layers. Any shape can be used for the porous electrolyte 20, solid electrolyte 12, and protective material 42, since the size and geometry of the various inserts, and therefore the corresponding openings, are dependent upon the desired size and geometry of the adjacent electrodes. It is preferred that the openings, inserts, and electrodes have a substantially similar geometry.

Dielectric layers 14, 22, 26, as well as support layers 30, 32, 34, 36 and outer layer, 40, are materials which effectively protect various portions of sensor element 10, provide structural integrity, and separate various components. Outer layer 40 and protective material 42 electrically isolate heater 38 from the sensor circuits, while support layers 30, 32, 34, 36 physically cover outer electrode 24 and heater 38. Dielectric layer 26 covers lead 46. Layers 26, 30, 32, 34, 36, 40 together with protective material 42 provide physical protection against abrasion and electrically isolate the components of sensor element 10 from the packaging. Preferably, as stated above, layers 14, 22, 26, 30, 32, 34, 36, 40 comprise alumina or similar materials, which are chosen to at least minimize, if not eliminate, delamination and other processing problems.

Layers 14, 22, 26, 30, 32, 34, 36, 40 can each be up to about 200 microns thick, with a thickness of about 50 microns to about 200 microns preferred. As with the solid and porous electrolytes, these layers can be formed using ceramic tape casting methods or other methods such as plasma spray deposition techniques, screen printing, stenciling and others conventionally used in the art.

Disposed between two of the substrate layers 36 and 40 is heater 38, with a ground plane (not shown) optionally disposed between two other substrate layers. Heater 38 can be any conventional heater capable of maintaining sensor end 50 of sensor element 10 at a sufficient temperature to facilitate the various electrochemical reactions therein. Heater 38, which is platinum, alumina, palladium, or the like, as well as mixtures and alloys comprising at least one of the foregoing, or any other conventional heater, is generally screen printed onto a substrate to a thickness of about 5 microns to about 50 microns.

Leads 46 are disposed across various dielectric layers 14, 22, 26 to electrically connect the external wiring of sensor element 10 with electrodes 16, 18, 24. Leads 46 are typically formed on the same layer as the electrode to which they are in electrical communication and extend from the electrode to the terminal end 48 of the element where they are in electrical communication with the corresponding via 44. Heater 38 also has leads that are in electrical communication with vias 44.

At terminal end 48 of sensor element 10, vias 44 are formed as holes filled with electrically conductive material in the appropriate layers 14, 22, 26, 40. Vias 44 are typically filled during formation of electrodes 16, 18, 24 and leads 46, and serve to provide a mechanism for electrically connecting leads 46 and heater 38 to the exterior of sensor element 10. Vias 44 are in electrical communication with contact pads (not shown), which are formed on the exterior surface of layers 26, 40. The contact pads provide a contact point for the external sensor circuit.

Disposed on the outer surface of at least a portion of the protective material 42, optionally over dielectric layer 26 and also optionally over protective outer layer 40, is an inhibitive coating 28 comprising an alkaline material and optionally alumina. Optionally, disposed between the protective material 42, layers 26, 40, and the inhibitive coating 28 can be spinel.

Inhibitive coating 28 can be any material that is capable of limiting the formation of dense glass phases that result from the reaction of metallic oxide particles with acid gases in the exhaust stream. Inhibitive coating 28 comprises a sufficient amount of a reactive material such that particles are formed and can precipitate out of the gas phase. The preferred inhibitive coating 28 is an alkaline earth material such as an ethoxide, carbonate, or oxide of an alkaline earth metal. This alkaline earth material is preferably deposited over a protective coating of alumina, with deposition over gamma alumina especially preferred. The alkaline earth coating prevents formation of phosphate ($PO_4^{2-}$) glasses that limit diffusion to the electrode by forming amorphous powder coatings that do not limit diffusion.

High concentrations of Group I and Group II (of the periodic table) elements may be used to form the materials that inhibit glass formation, e.g., oxides, carbonates, and the like, as well as combinations comprising at least one of the foregoing. Preferred alkaline earth oxides are those formed from the elements found in Group II of the Periodic Table. The most preferred alkaline earth oxide is that containing the largest cation (i.e., barium oxide (BaO)). Other alkaline earth oxides that may be used and that are formed from Group II elements include strontium oxide (SrO), calcium oxide (CaO), and magnesium oxide (MgO), with calcium oxide being more preferred than magnesium oxide, and strontium oxide being more preferred than calcium oxide.

Group I elements are less preferred for forming the oxides than are Group II elements. Of the Group I elements that may be used, those having the largest cations are the most preferred, i.e., cesium oxide ($Cs_2O$). Other Group I oxides that may be used include potassium oxide ($K_2O$), sodium oxide ($Na_2O$), lithium oxide ($LiO_2$), and the like, as well as combinations comprising at least one of the foregoing oxides, with sodium oxide being more preferred than lithium oxide, and potassium oxide more preferred than sodium oxide.

In addition to the oxides, alkaline earth carbonates may also be employed. For example, barium carbonate ($BaCO_3$), strontium carbonate ($SrCO_3$), calcium carbonate ($CaCO_3$), magnesium oxide ($MgCO_3$), and the like may be used. The alkaline earth materials (oxides, carbonates, and others) may each be used alone, as well as in combinations comprising at least one of the foregoing alkaline earth materials.

Other materials that may be used include minerals, which may have high concentrations of alkaline earths. These minerals include, but are not limited to, dolomites, magnesites, lansfordite, artinite, aragonite, calcite, strontianite, witherite, talc, steatite, fluorspar, kaolin, borax, spodumene, wollastonite, and the like, as well as in combinations comprising at least one of the foregoing minerals.

In order to correct lean shift and/or inhibit poisoning by carbon monoxide adsorption, inhibitive coating 28 may also comprise a material that comprises a precious metal (e.g., platinum (Pt), palladium (Pd), rhodium (Rh), osmium (Os), iridium (Ir), ruthenium (Ru), gold (Au), and the like as well as combinations comprising at least one of the foregoing metals) and/or a CO inhibitor such as lead (Pb). The material may be calcium carbonate comprising Pd, Rh or Pt for lean shift correction. Generally, up to about 10 wt % precious metal and up to 8 wt % lead, with about 0.5 wt % to about 7 wt % precious metal and about 0.05 wt % to about 5 wt % lead preferred, and about 2 wt % to about 6 wt % precious metal and about 0.5 to about 4 wt % lead, balance alkaline earth material, especially preferred, can be employed based upon the combined weight of the alkaline earth material, precious metal, and CO inhibitor.

For example, the combined formulation could comprise $CaCO_3$ with 5 wt % Pd and 3.5 wt % Pb. The $CaCO_3$/Pd/Pb can be formed by reacting non-acidic palladium and lead salts with calcium carbonate. When exposed in the exhaust stream to phosphate acid gasses, the $CaCO_3$/Pd/Pb will form a lead and palladium doped calcium hydroxyapatite catalyst such that the Pd and Pb are trapped in the lattice points of calcium defects.

The limiting of the formation of the dense glass phases on sensor element 10 is achieved by ensuring that an excess amount of alkaline earth material is deposited on sensor element 10 as inhibitive coating 28. An excess amount of alkaline earth material is that amount that inhibits the formation of a dense glass phase over sensor element 10 for a period of time of actual engine use. Preferably, the formation of dense glass phases over sensor element 10 during engine use should be inhibited for at least about 1,000 hours, with at least about 2,000 hours being preferred, and with at least about 3,000 hours being especially preferred. For accelerated aging with poisons present in the exhaust gas, the formation of dense glass phases should be inhibited for at least about 100 hours, with at least about 150 hours preferred, and at least about 200 hours especially preferred.

In order to be effective, inhibitive coating 28 has a thickness of about 5 um (microns) to about 25 um, with a thickness of about 10 um to about 20 um being preferred. Typically, about 10 mg or greater per part to be coated is used, with about 20 mg or greater per part being preferred, and about 30 mg or greater per part being especially preferred.

The inhibitive coating 28 can be applied by any conventional technique, such as spraying, vapor deposition, painting, dipping, and the like. One method of applying inhibitive coating 28 for example, involves disposing a wet alumina slurry over a spinel porous protective layer. The wet layer is then exposed to dry palladium doped $CaCO_3$ particles. The dry palladium doped $CaCO_3$ particles stick to the surface of the wet layer, which is then dried and calcined at 500° C. to produce an outer "layer" of coarse calcium oxide particles protruding through an alumina layer.

Another method of applying the alkaline material to sensor element 10 comprises dipping sensor element 10 into a slurry of coarse palladium doped calcium oxide and water. Here, sensor element 10 already has a spinel layer disposed over outer electrode 24 and an alumina layer disposed over the spinel layer. Sensor element 10 is then optionally dipped into a suspension of calcium oxide particles. The resulting sensor element 10 includes two distinct layers, the bottom layer being alumina oxide and the top layer being calcium oxide and palladium.

Sensor element 10 described above comprises inhibitive coating 28, which comprises a layer of excess alkaline earth material which facilitates the formation of particulates that readily precipitate out of the exhaust gas. These materials combine with the phosphates in the exhaust gas to form alkaline earth rich phosphate particles on the surface of the porous protective coatings. Without inhibitive coating 28 (or with an inhibitive coating that is inadequate for the formation of the large particles), phosphates in the exhaust gas combine with metallic or metallic oxide, particulates (such as calcium, zinc, and the like) also in the exhaust gas to form compounds such as $CaPO_4$, $Zn_3(PO_4)_2$, $Ca_2P_2O_6$, $Ca_2P_2O_7Ca(PO_3)_2$, $Zn_2P_2O_7$, mixed $CaZnP_2O_6$, and the like, which are deposited on sensor element 10 as dense glass phases.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

We claim:

1. An exhaust gas sensor element comprising:

an electrochemical cell;

a protective material in fluid communication with the electrochemical cell; and an inhibitive coating disposed on a side of the protective material opposite the electrochemical cell, the inhibitive coating comprising an alkaline material selected from the group consisting of Group I oxides, Group I carbonates, kaolin, borax, spodumene, and combinations comprising at least one of the foregoing materials.

2. The exhaust gas sensor element of claim 1, wherein the inhibitive coating further comprises a precious metal.

3. The exhaust gas sensor element of claim 2, wherein the precious metal is selected from the group consisting of platinum, palladium, rhodium, iridium, ruthenium, osmium, gold, and combinations comprising at least one of the foregoing metals.

4. The exhaust gas sensor element of claim 2, wherein the inhibitive coating further comprises a carbon monoxide adsorption inhibitor.

5. The exhaust gas sensor element of claim 4, wherein the carbon monoxide adsorption inhibitor is lead.

6. The exhaust gas sensor element of claim 1, wherein the inhibitive coating has a thickness of about 5 microns to about 25 microns.

7. The exhaust gas sensor element of claim 6, wherein the inhibitive coating has a thickness of about 10 microns to about 20 microns.

8. The exhaust gas sensor element of claim 1, wherein the inhibitive coating further comprises about 0.5 wt % to about 7 wt % precious metal and about 0.05 wt % to about 5 wt % lead, balance being the alkaline material.

9. The exhaust gas sensor element of claim 8, wherein the inhibitive coating comprises about 2 wt % to about 6 wt % of the precious metal and about 0.5 wt % to about 4 wt % of the lead, balance being the alkaline material.

10. A method of operating a gas sensor, comprising: exposing the gas sensor to an exhaust gas wherein the gas sensor comprises, an electrochemical cell, a protective material in fluid communication with the electrochemical cell, and an inhibitive coating disposed on a side of the protective material opposite the electrochemical cell, the inhibitive coating comprising an alkaline material selected from the group consisting of Group I oxides, Group I carbonates, kaolin, borax, spodumene, and combinations comprising at least one of the foregoing materials;

diffusing the exhaust gas through the inhibitive coating to the electrochemical cell;

sensing a constituent of the gas; and reacting acid gases in the exhaust gas with the inhibitive coating.

11. The method of operating a gas sensor of claim 10, wherein the inhibitive coating further comprises about 0.5 wt % to about 7 wt % precious metal and about 0.05 wt % to about 5 wt % lead, balance being the alkaline material.

12. The method of operating a gas sensor of claim 11, wherein the inhibitive coating comprises about 2 wt % to about 6 wt % of the precious metal and about 0.5 wt % to about 4 wt % of the lead, balance being the alkaline material.

* * * * *